US 8,083,683 B2

(12) United States Patent
Lane et al.

(10) Patent No.: US 8,083,683 B2
(45) Date of Patent: Dec. 27, 2011

(54) DUAL LUMEN INTERCHANGEABLE MONITOR SYSTEM

(75) Inventors: John A. Lane, Weedsport, NY (US);
Scott A. Martin, Warners, NY (US);
William J. Smirles, Deerfield, IL (US);
Braxton Lathrop, Lake Oswego, OR (US); Andrew M. Robottom, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1102 days.

(21) Appl. No.: 11/875,167

(22) Filed: Oct. 19, 2007

(65) Prior Publication Data
US 2009/0105599 A1    Apr. 23, 2009

(51) Int. Cl.
*A61B 5/02* (2006.01)
(52) U.S. Cl. ........................................ 600/490; 600/485
(58) Field of Classification Search .................. 600/481, 600/485, 490, 492–499; 73/862, 862.381, 73/862.581–862.583; 606/201–203
See application file for complete search history.

(56) References Cited

U.S. PATENT DOCUMENTS

| | | | |
|---|---|---|---|
| 3,229,721 A | 1/1966 | Bingel | |
| 4,821,774 A * | 4/1989 | Chorkey | 137/625.65 |
| 4,953,557 A | 9/1990 | Frankenreiter et al. | |
| 4,971,063 A * | 11/1990 | Flachslaender et al. | 600/490 |
| 5,464,019 A * | 11/1995 | Anderson et al. | 600/490 |
| 6,450,966 B1 * | 9/2002 | Hanna | 600/490 |
| 6,582,374 B2 | 6/2003 | Yokozeki | |
| 7,226,419 B2 * | 6/2007 | Lane et al. | 600/490 |
| 7,429,245 B2 * | 9/2008 | Whitaker et al. | 600/494 |
| 2003/0093001 A1 * | 5/2003 | Martikainen | 600/499 |
| 2004/0244850 A1 * | 12/2004 | Browne et al. | 137/625.5 |
| 2005/0033188 A1 | 2/2005 | Whitaker et al. | |
| 2006/0293601 A1 * | 12/2006 | Lane et al. | 600/495 |

OTHER PUBLICATIONS

International Search Report and Written Opinion of the International Searching Authority, mailed Mar. 27, 2009, International Application No. PCT/US2008/079820 (12 pages).

Degrees of Protection Provided by Enclosures (IP code); British Standard, BS EN 60529:1992, Incorporating Amendments Nos. 1 and 2; (43 pages).

* cited by examiner

*Primary Examiner* — Miranda Le
*Assistant Examiner* — Meredith Weare

(57) ABSTRACT

A flow system for use in a monitor for measuring blood pressure that automatically configures the flow path of the system when either a single lumen cuff or a dual lumen cuff is coupled to the monitor.

15 Claims, 8 Drawing Sheets

DUAL LUMEN INTERCHANGEABLE MONITOR SYSTEM

FIELD OF THE INVENTION

This invention relates generally to a blood pressure monitor and, in particular, to a monitor for measuring a patients blood pressure when taken using either a single lumen inflatable cuff or a dual lumen inflatable cuff.

BACKGROUND OF THE INVENTION

Non-invasive blood pressure monitors are widely used in hospitals and other clinical facilities to measure the blood pressure of patients. In this procedure an inflatable cuff is wrapped about the patients arm or leg and is inflated to a predetermined pressure over an artery. When employing a single lumen cuff, the systolic and diastolic measurements are taken as the cuff is being deflated. A more recent procedure has been developed wherein the pressure measurements are taken during the period when the cuff is being inflated. This later procedure allows for a more rapid determination of the patients blood pressure which in certain cases, can be extremely important. A dual lumen cuff is required to carry out this more rapid procedure.

In U.S. Pat. No. 7,226,419 B2 to Lane et al. there is disclosed a blood pressure monitor that has the capability of taking blood pressure measurements involving the more rapid procedure requiring the use of a dual lumen cuff or, alternatively, the slower, more conventional, procedure using a single lumen cuff. As explained in greater detail in the Lane et al. patent the monitor contains a pair of pneumatic flow circuits and a pair of lumen connector terminals. The terminals are mounted upon an outer wall of the monitor cabinet and are arranged to interchangeably accept one of two available flow adaptors. The first adaptor is configured to accept the one lumen of a single lumen cuff and place the lumen in fluid flow communication with both flow circuits. The second adaptor is configured to individually accept each of the two lumens of a dual lumen cuff and place each lumen in fluid flow communication with a separate one of the two flow circuits. The adaptors, however, must be changed manually to accommodate an appropriate connection. The manual changing of adaptors can be a time consuming process particularly during a medical emergency where loss of time may be critical. In addition, the adaptors can easily become lost or be inadvertently carried off to an unknown location again extending the amount of time needed to change the monitor over from one of the two available measurement configuration to another.

SUMMARY OF THE INVENTION

It is therefore an object of the present invention to improve blood pressure monitors.

It is a further object of the present invention to provide a blood pressure monitor capable of employing both a single or dual lumen cuff without the need of manually changing cuff adaptors.

A still further object of the present invention is to provide a blood pressure monitor that is capable of accepting either a single lumen cuff or a dual lumen cuff and automatically configuring the pneumatic system to carry out either a fast or non-fast measurement procedure depending upon the particular cuff geometry.

These and other objects of the present invention are attained by a blood pressure monitor for measuring a patients blood pressure that will accept either a single lumen cuff or a double lumen cuff and will automatically configure the pneumatic flow systems to measure the patient's blood pressure accordingly without the need of special easily lost interchangeable adaptors.

BRIEF DESCRIPTION OF THE DRAWINGS

For a better understanding of these and other objects of the present invention, reference will be made to the following detailed description of the invention which is to be read in association with the accompanying drawings wherein.

DETAILED DESCRIPTION

Figure 1:
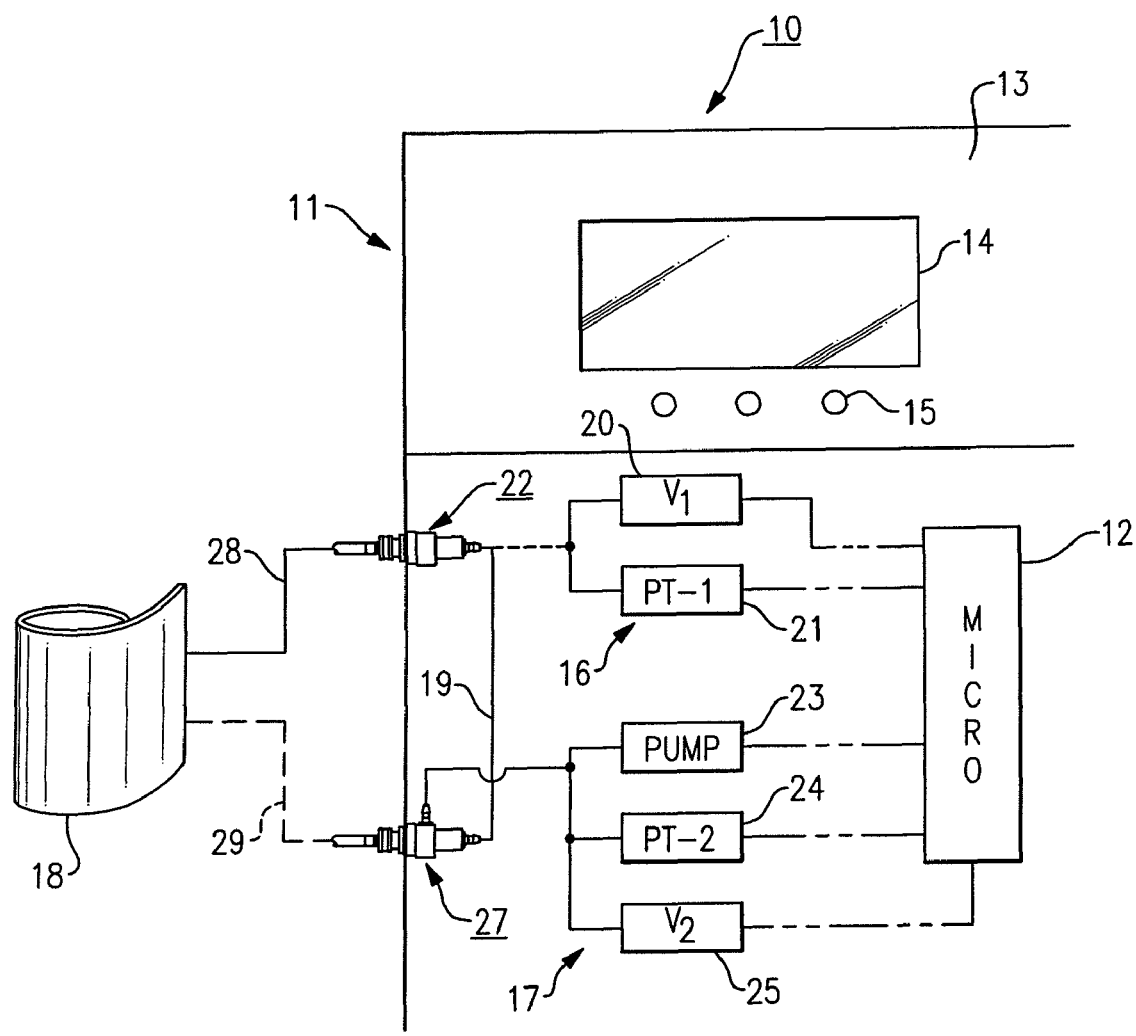
FIG. 1 is a schematic representation of a first embodiment of the invention illustrating a blood pressure monitor having two lumen input terminals and a pneumatic flow system that is automatically configured to provide blood pressure measurement when either a single lumen cuff or a dual lumen cuff is connected to the monitor.

Referring initially to FIGS. 1-5, there is illustrated a first embodiment of the present invention that relates to a medical blood pressure monitor generally referenced 10, for measuring a patient's blood pressure. As noted above, the monitor is described in greater detail in the Lane et al. patent and this description is herein incorporated by reference. The monitor includes a housing 11 that contains a microprocessor 12 and an interface section 13 having a visual display 14, and a plurality of input keys 15-15. The microprocessor, among other things controls a pair of pneumatic flow circuits, generally referenced 16 and 17, for inflating and deflating a blood pressure cuff 18 to determine the patient's blood pressure. The measuring blood pressure readings can be visually displayed upon the screen along with other related data. As disclosed in the Lane et al. patent, the microprocessor is configured to measure a patient's blood pressure during the cuff inflation period of the measuring cycle when a dual lumen cuff is connected to the monitoring system and to measure the patient's blood pressure during the cuff deflation period when a single lumen cuff is connected to the monitoring system.

The first flow circuit 16 includes at least a safety valve 20 for exhausting the system under certain adverse conditions and a pressure sensor 21 for providing pressure data relating to flow circuit 1. The first circuit is directly coupled to a first flow terminal 22. The second flow circuit 17 includes at least a pneumatic pump 23 for inflating a cuff, a second pressure sensor 24 and a bleed valve 25 for deflating a cuff. The second circuit is directly coupled to a second flow terminal 27. The flow terminals are mounted in one side wall of the monitor housing and enabling the monitor to be connected to either a single lumen cuff or a dual lumen cuff. As depicted by the phantom lines in FIG. 1 each of the circuit elements are electrically coupled to the microprocessor so that sufficient control data can be exchanged between each of the circuit elements and the microprocessor to obtain blood pressure readings from either a single lumen cuff or a dual lumen cuff.

Figure 4:
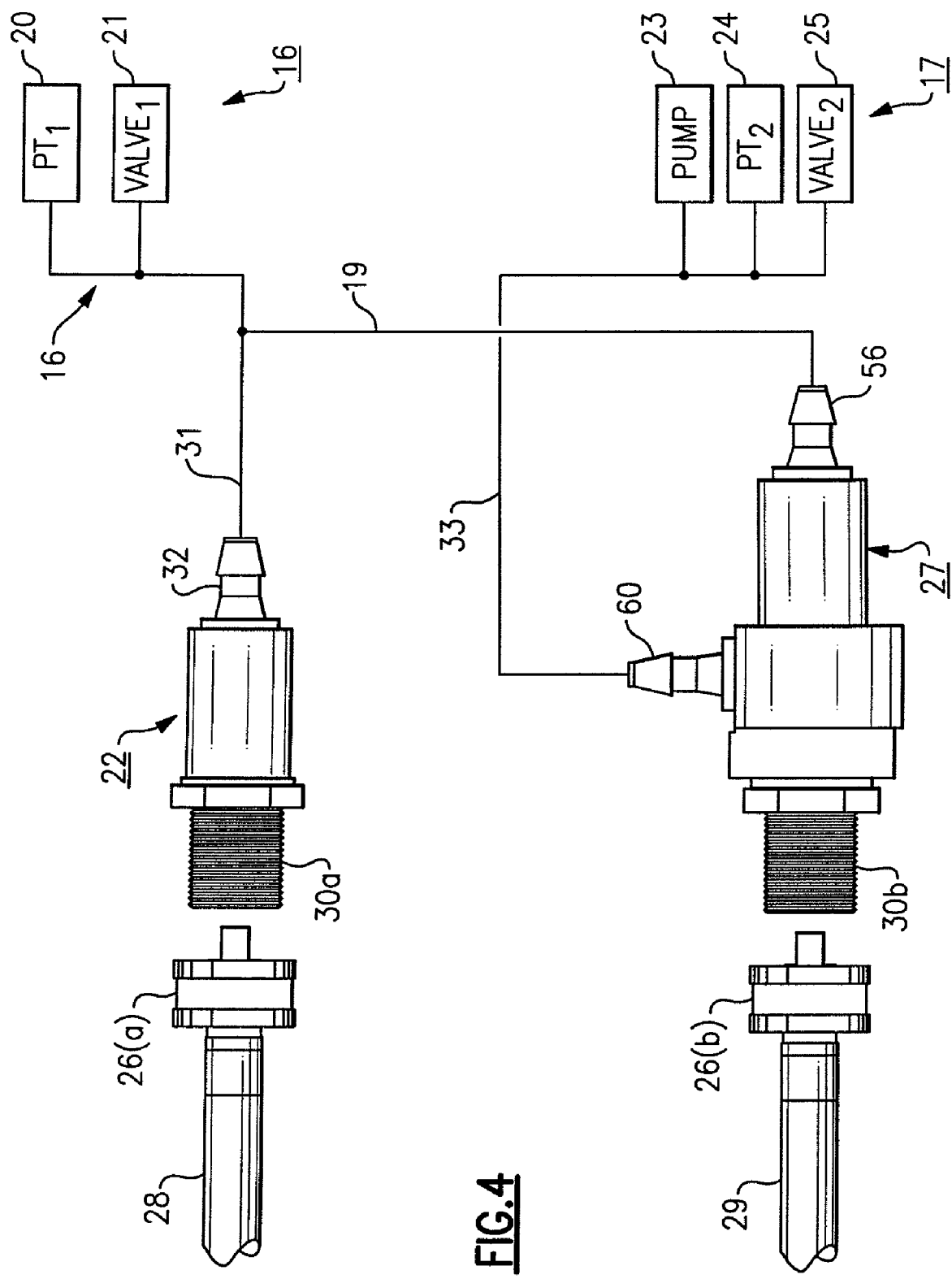
FIG. 4 is an enlarged schematic view of the monitors pneumatic flow circuit wherein one of the lumen input terminals is equipped with an automatically actuated flow director.

As best illustrated in FIG. 4, each flow terminal is provided with a threaded end 30(*a*) and 30(*b*). Terminal 22 has a straight through flow path. Lumen 28, which may be the only lumen of a single lumen cuff or one of the two lumens of a dual lumen cuff may be coupled to the threaded end 30(*a*) of the terminal 22 by a connector 26(*a*). First flow circuit 16 is placed in communication with terminal 22 by coupling flow line 31 to the terminal 22. A second lumen 29 of a dual lumen cuff may be coupled to the threaded end of the second terminal 27 by means of a second connector 26(*b*). Terminal 27 includes a three-way valve having a pair of nipples 56 and 60. Nipple 56 is coupled directly to the first flow circuit 16 via shunt line 19 while nipple 60 is connected to the second flow circuit 17, which contains pneumatic pump 23 by means of flow line 33. The pump is thus arranged to deliver air under pressure into the terminal 27 via nipple 60.

As will be explained in greater detail below the terminal 27 is equipped with a flow diverter network that can selectively direct air from the pump into shunt line 19 or alternatively into lumen 29 via connector 26(*b*) when the connector is coupled to the threaded end of the terminal. Accordingly, when a single lumen cuff is connected to terminal 22 and no second lumen is connected to terminal 27, air flowing from the pump is diverted to shunt line 19 and then through lumen 28 to the cuff whereupon the cuff is inflated. Blood pressure readings are then taken in a conventional manner as the cuff is being deflated through lumen 28 as the bleed valve 21 is cycled. Connecting a second lumen 29 to terminal 27 will automatically cause the flow diverter network to change its operational mode wherein air from the pump is sent to the cuff through lumen 29 to inflate the cuff. The cuff is then deflated in this mode back through lumen 29. As explained in greater detail in the above noted Lane et al. patent, blood pressure readings can be taken rapidly during cuff inflation when the flow system is in this configuration.

Figure 2:
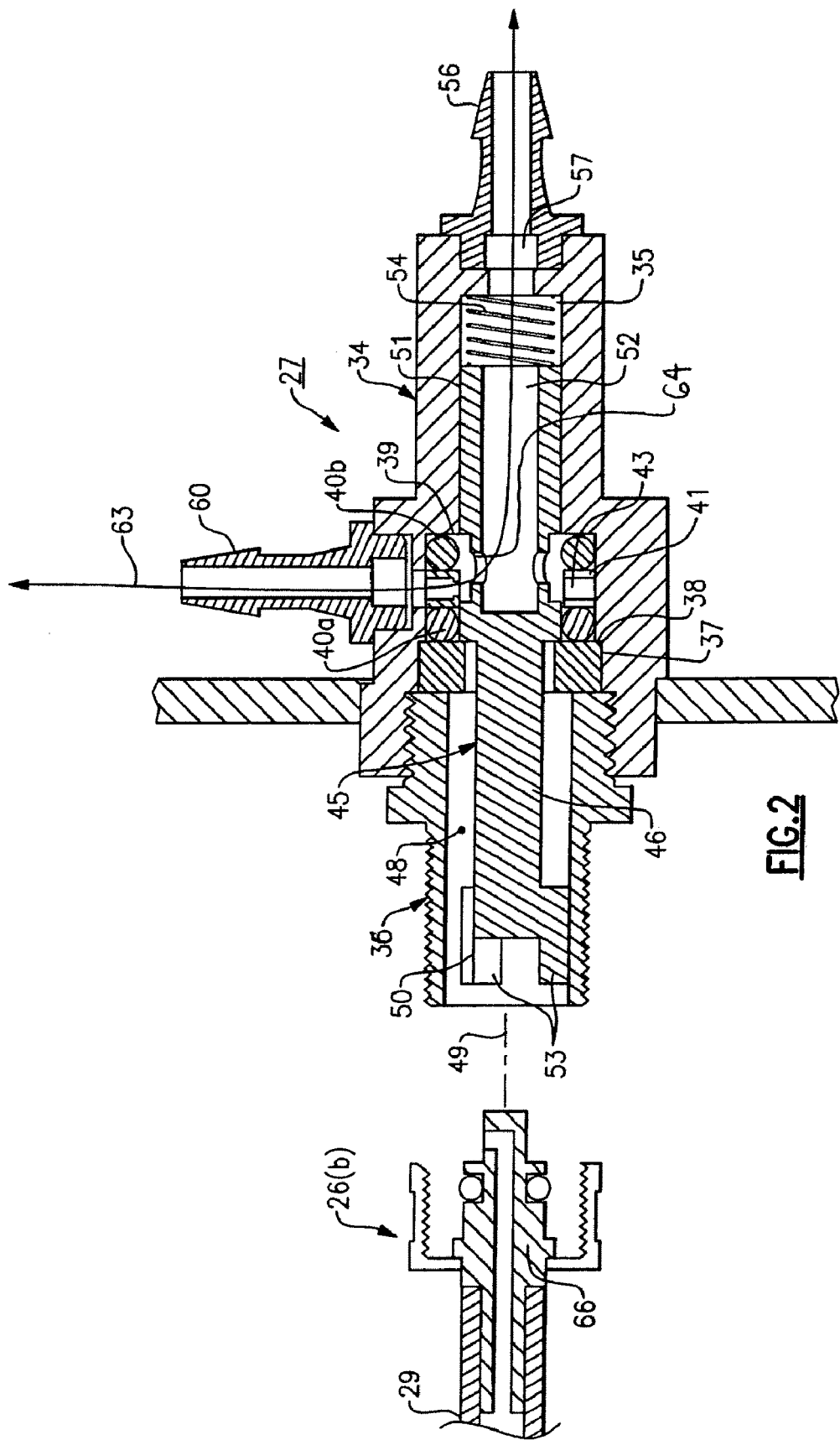
FIG. 2 is a an enlarged side view in section illustrating one of the lumen input terminals shown in FIG. 1 in a first operational mode when a single lumen cuff is connected to the monitor.
Figure 3:
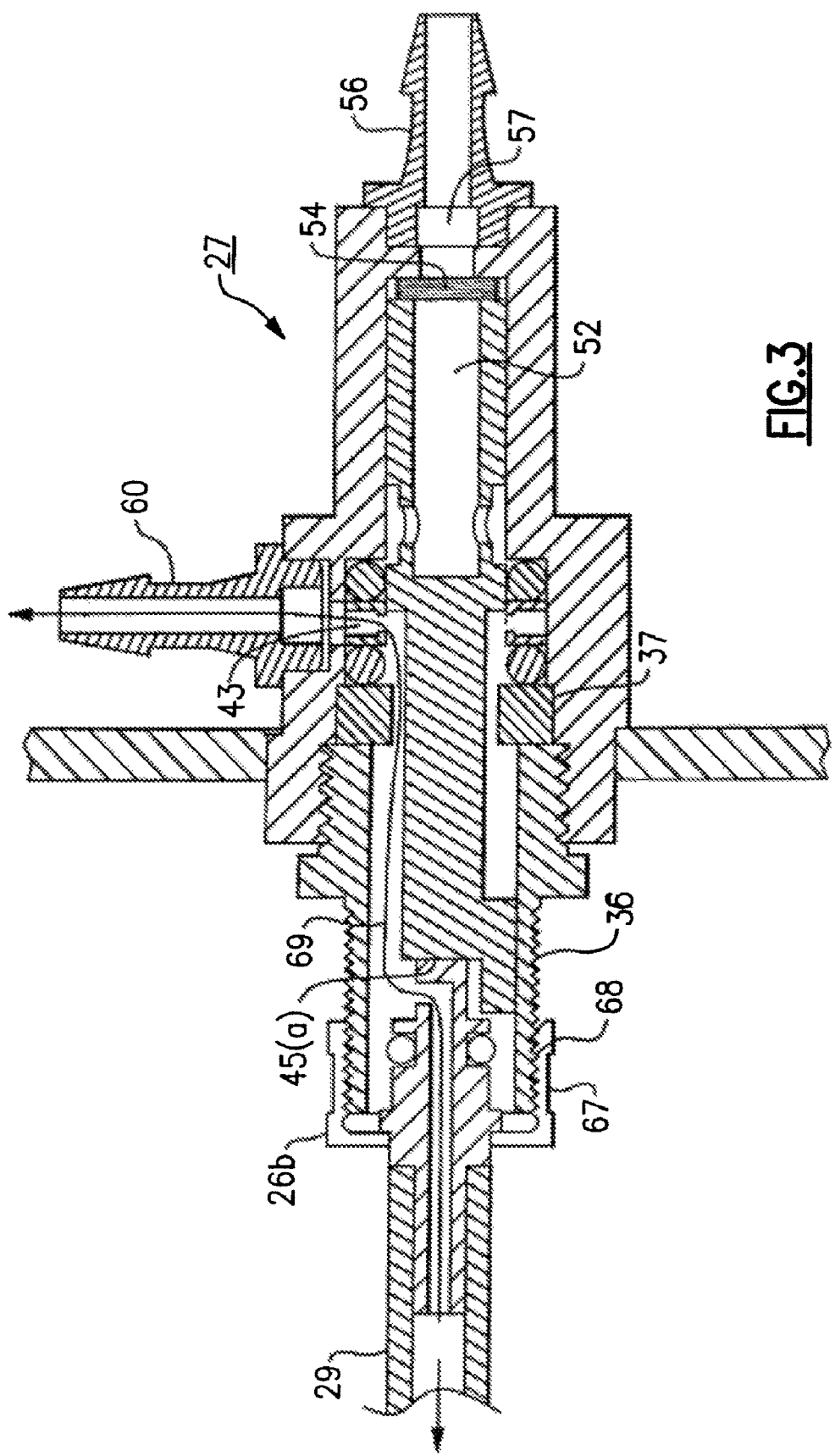
FIG. 3 is an enlarged side view in section illustrating the lumen input terminal shown in FIG. 2 in a second operational mode of operation when a dual lumen cuff is connected to the monitor.

Turning now to FIGS. 2 and 3, terminal 27 is illustrated in greater detail. FIG. 2 which depicts the terminal in a first mode of operation wherein a first lumen 28 is connected to terminal 22 and wherein terminal 27 is not connected to a second lumen which is the case when a single lumen cuff has been employed. Lumen input terminal 27 includes a main body section 34 that contains a circular opening 35 that passed there through. An end adaptor 36 is threaded into one end of the body section which contains an opening 48 that is in axial alignment with the body opening 35 and is in communication therewith. In assembly, the adaptor is arranged to hold a washer 37 tightly against a shoulder 38 formed in a main body opening. The washer is located immediately adjacent to a radially expanded recess 39 contained in an opening 35. A pair of O-ring seals 40(*a*) and 40(*b*) mounted in the recess and are separated by an annular spacer 41 which has a series of holes 43-43 circumferentially spaced thereabout.

An elongated piston, generally referenced 45, is slidably contained within the terminal 27. The piston includes a solid proximal end section 46 that is housed generally within the adaptor and which extends back into the main body opening. The opposite or distal end 51 of the piston is cylindrical and contains a blind hole 52. A series of flutes 53-53 are mounted on the proximal end of the piston which are arranged to ride against the inner wall of the adaptor to hold the piston centered along axis 49 of the adaptor. A compression spring 54 is mounted in housing opening 35 adjacent to the distal end of the piston and is arranged to bias the piston outward against the washer 37.

A hollow nipple 56 is press fitted into one end of the terminal body adjacent the biasing spring and communicates with the body opening through channel 57. As illustrated in FIG. 2 the connector 26(*b*) is shown disconnected from the terminal. At this time the piston is biased by spring 54 back against the washer 37. A second hollow nipple 60 is press fitted into the terminal body directly over the expanded recess 39 of the central opening in the housing body. The nipple 60 is arranged to open into the recess. As illustrated in FIG. 4, nipple 56 is coupled to flow circuit 16 via flow line 19 and nipple 60 is coupled to flow circuit 17 via shunt line 33. Accordingly, when a lumen is not connected to the terminal 29 the flow path 63 (FIG. 2) through the terminal passes from the nipple 56 through the hollow bore of the piston and exits through an opening 64 in the piston and out the nipple 60 via the holes in the spacer 41. As can be seen, this closes the adaptor opening 48 and places flow circuits 17 in direct communication with flow circuit 16 via flow line 19. Accordingly, the monitor flow system is now configured to measure blood pressure in association with a single lumen cuff wherein the cuff is inflated and deflated through lumen 28 and blood pressure is measured during the deflation part of the cycle.

As illustrated in FIG. 3, the connector 26(*b*) of lumen 29 has a cap 67 containing internal threads 68 that mate with the external thread upon the adaptor 36 of the terminal 27. The connector further includes an extended member 66 that protrudes outwardly from the cap and is arranged to contact the proximal end 45(*a*) of the piston 45. As the end cap is threaded onto the adaptor, the piston is pushed back against the biasing pressure of the spring 54 thus closing off the blind hole in the distal end of the piston to terminate the flow path between the two nipples 56 and 60. A new flow path 69 is now established between nipple 60 and the lumen connector 29 via the opening in the terminal body and the adaptor. This, in term, configures the monitor flow system to take blood pressure readings using a dual lumen cuff wherein the cuff is inflated and deflated through lumen 29 and pressure is measured through lumen 28 (FIG. 1).

Figure 5:
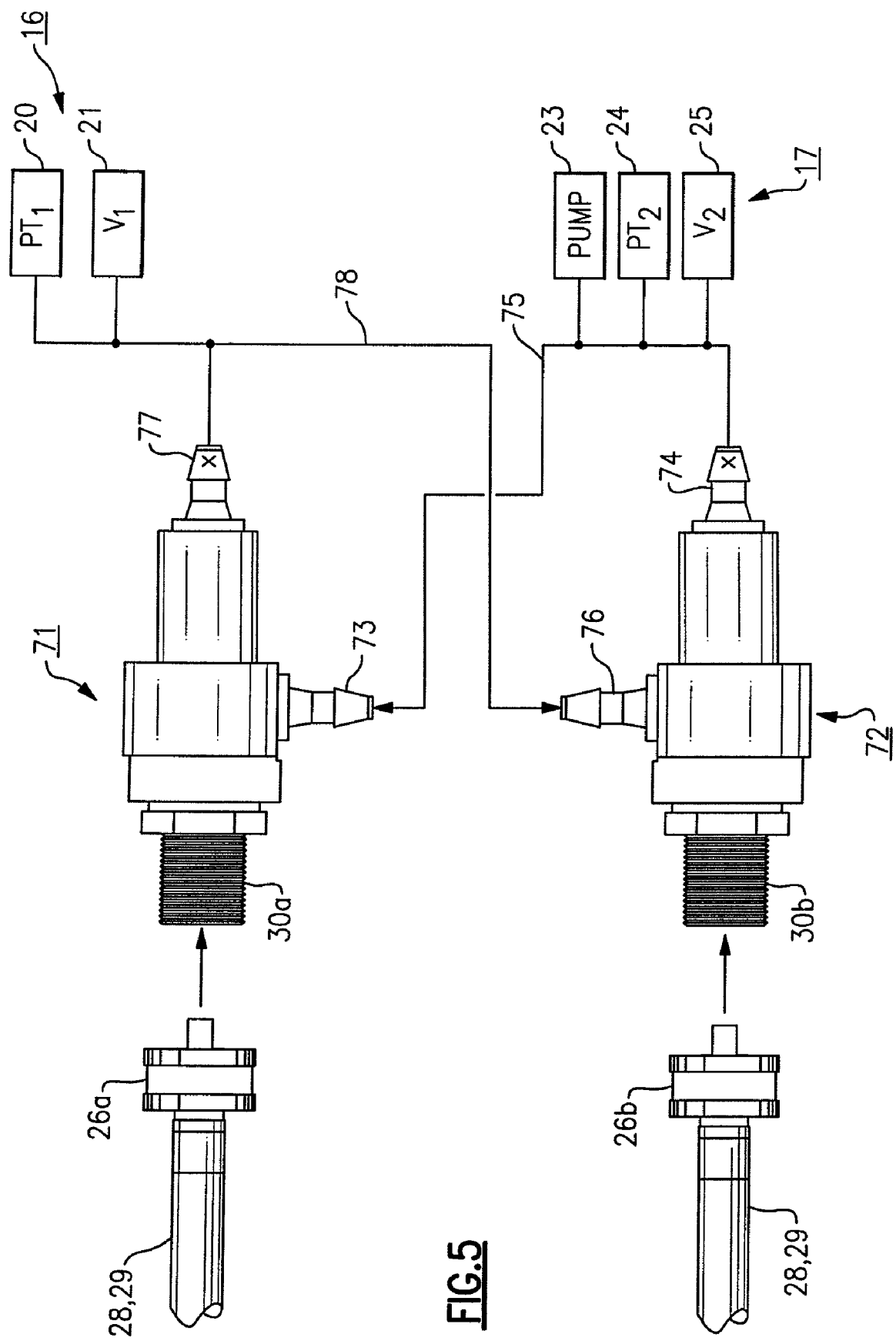
FIG. 5 is also an enlarged schematic view similar to that shown in FIG. 4 wherein each of the lumen input terminals is equipped with an automatically actuated flow director.
Figure 6:
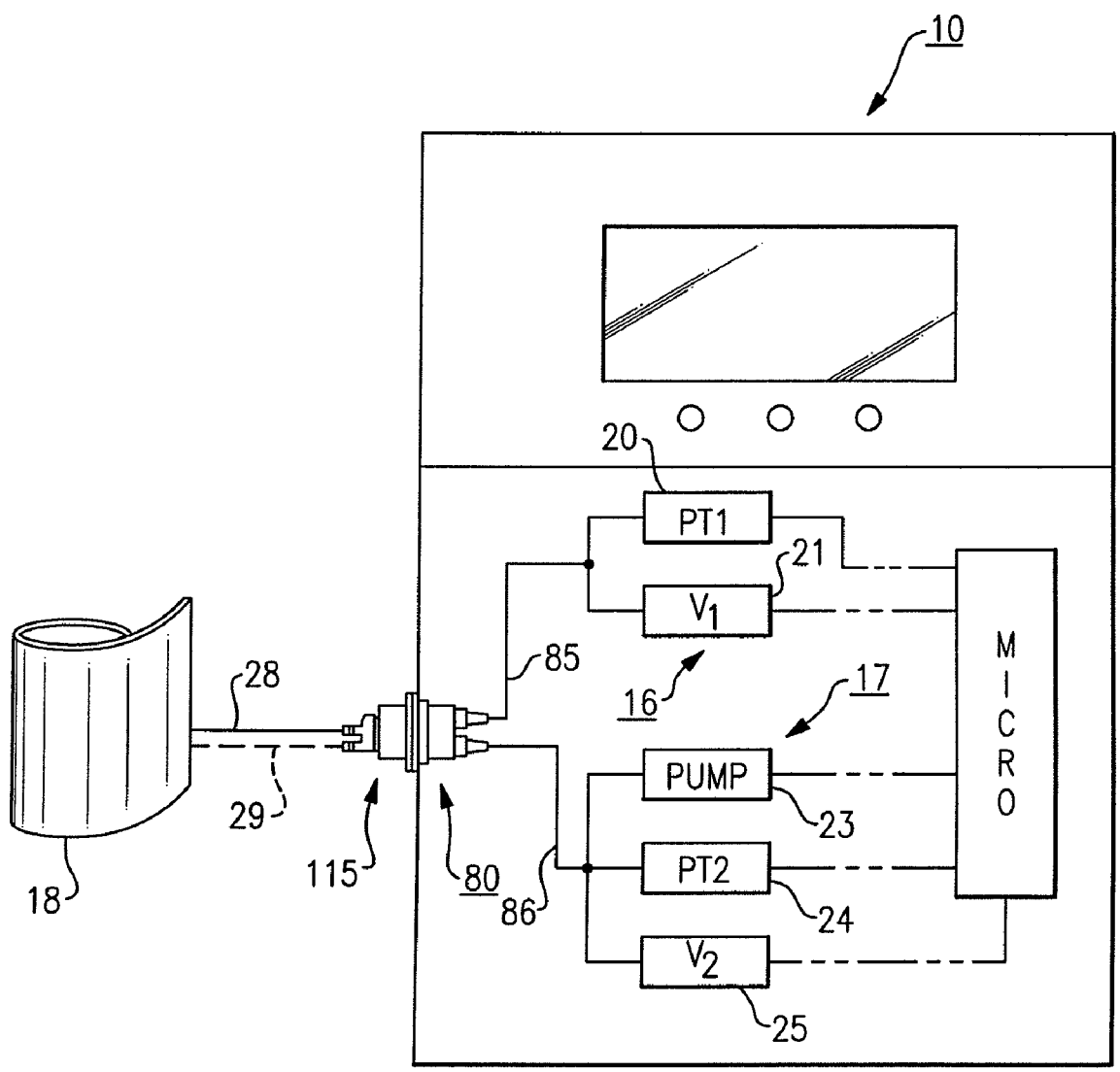
FIG. 6 is a schematic representation of a second embodiment of the invention illustrating a blood pressure monitor having a single lumen input terminal that can be connected to either a single lumen cuff or a dual lumen cuff so that the pneumatic system of the monitor is automatically configured to provide blood pressure measurement when either a single lumen or a dual lumen cuff is connected to the terminal and illustrating a single lumen cuff connected to the lumen input terminal.
Figure 7:
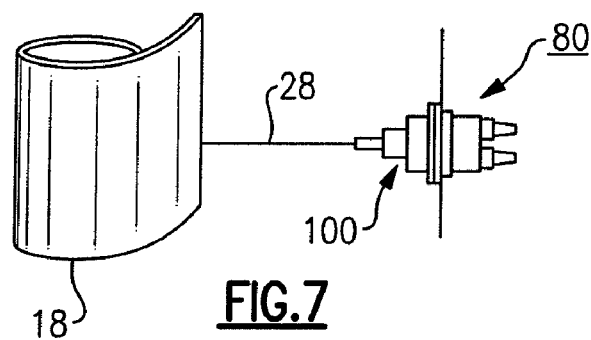
FIG. 7 is a partial view illustrating a dual lumen cuff connected to the single input terminal of FIG. 6.

FIG. 5 illustrates a flow system that is similar to that shown in FIG. 4, however in this embodiment, the flow system will automatically configure itself to enable blood pressure measurement to be taken regardless of how the lumens of a single lumen cuff or the lumens of a double lumen cuff are coupled to the two terminals. Accordingly, a technician using the monitor cannot make a faulty connection when using either a single lumen cuff or a double lumen cuff.

In this system arrangement each of the two lumen terminals 71 and 72 are equipped with a flow director network as described above with reference to terminal 27. In this arrangement nipple 73 of terminal 71 is connected to nipple 74 of terminal 72 and to flow circuit 17 by flow line 75. Nipple 76 of terminal 72, in turn, is connected to nipple 77 of terminal 71 and flow circuit 16 by flow line 78. As should be evident from the description above coupling a lumen of a single lumen cuff to either terminal will automatically configure the flow system to carry out a convention blood pressure measurement wherein the cuff will be inflated and deflated through the selected terminal. Coupling both lumen of a dual lumen cuff to the two terminals of monitor will again automatically configure the system so that the cuff is inflated and deflated through one lumen and pressure is measured through the other lumen. As described in the above noted Lane et al. patent, in this configuration, the monitor can rapidly take the measurement during the inflation phase of the blood pressure measurement cycle.

FIGS. 6-9 depict a further embodiment of the invention which employs a single lumen input terminal generally referenced 80 wherein like reference numbers are used to identify like components found in the first embodiment noted above. In this embodiment of the invention the input terminal 80 includes a body section 81 that has a pair of hollow nipples 82 and 83. Nipple 82 is coupled to the first flow circuit 16 by means of a flow line 85 and nipple 83 is likewise coupled to flow circuit 17 by means of flow line 86. Nipple 82 communicates with first cavity 87 in the body of the housing while nipple 83 communicates with a separate second cavity 88. Cavity 87 empties directly into a blind hole 90 that is bored into the terminal body from the side opposite the lumen nipples. Cavity 88 also empties into the blind hole via channel 91 and entranceway 92.

The terminal body includes a circular flange 95 that contains a male thread 96 formed thereon. A circular recess 97 passes into the flange which houses a threaded elongated member 98 that is integral with the body and which passes outwardly beyond the flange. The elongated member 98 is arranged to receive thereon a first single lumen connector generally referenced 100 having a rotatable cap 101 which mates with the threads on member 98. Threading the cap of the connector onto the member pulls the main section 102 of the connector into the blind hole of the terminal body.

Figure 8:
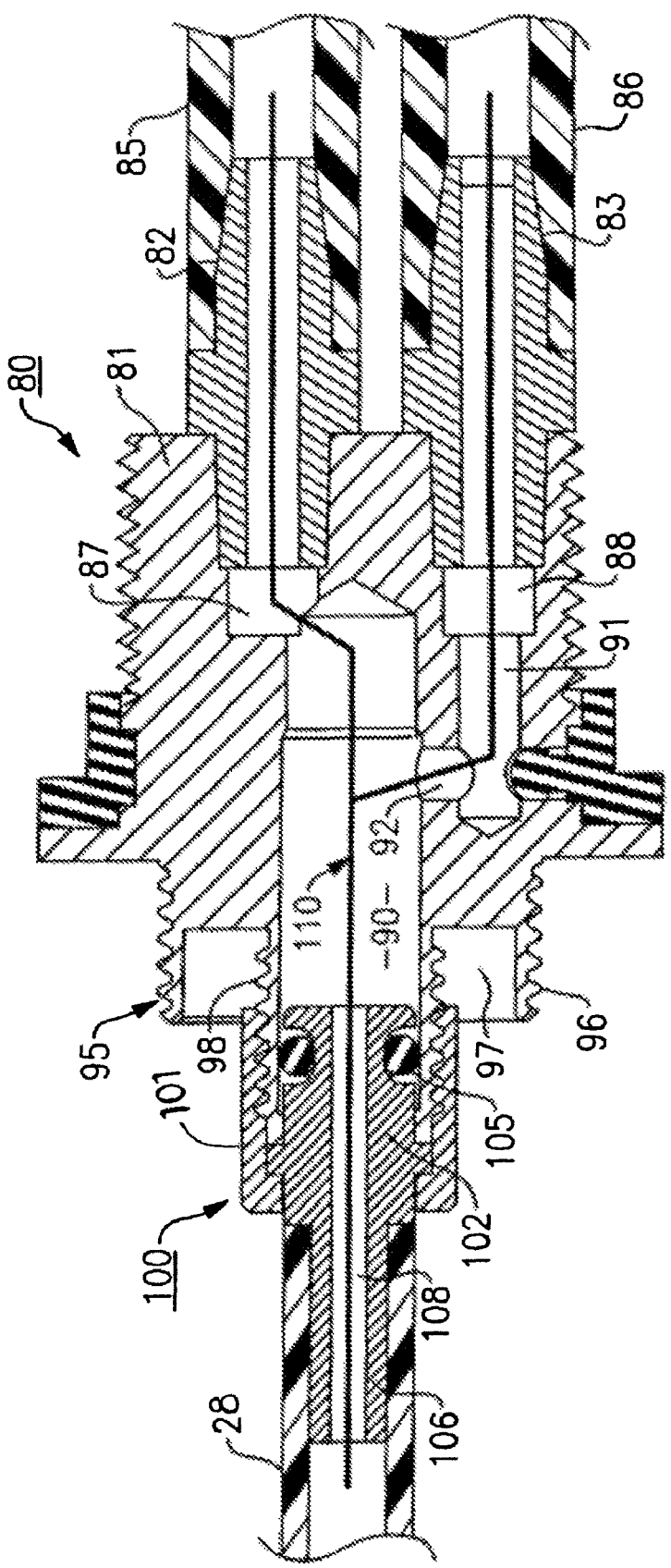
FIG. 8 is an enlarged side view in section showing the single lumen input terminal connected to a single lumen cuff.

The main section of the connector is equipped with an O-ring seal 105 that rides in sliding contact with the inner wall of the blind hole 90. The connector further contains a rearwardly extended section 106 upon which a single cuff lumen 28 is fitted. The connector contains a through hole 108 that passes through the center of the connector. When the connector 100 is mounted upon terminal 80 as shown in FIG. 8, a split flow path 110 is established that couples lumen 28 and flow lines 85 and 86 connecting together flow circuits 16 and 17 (see FIG. 6). The monitor is now in a configuration to take a patients blood pressure in conjunction with a single lumen cuff (see FIG. 7).

Figure 9:
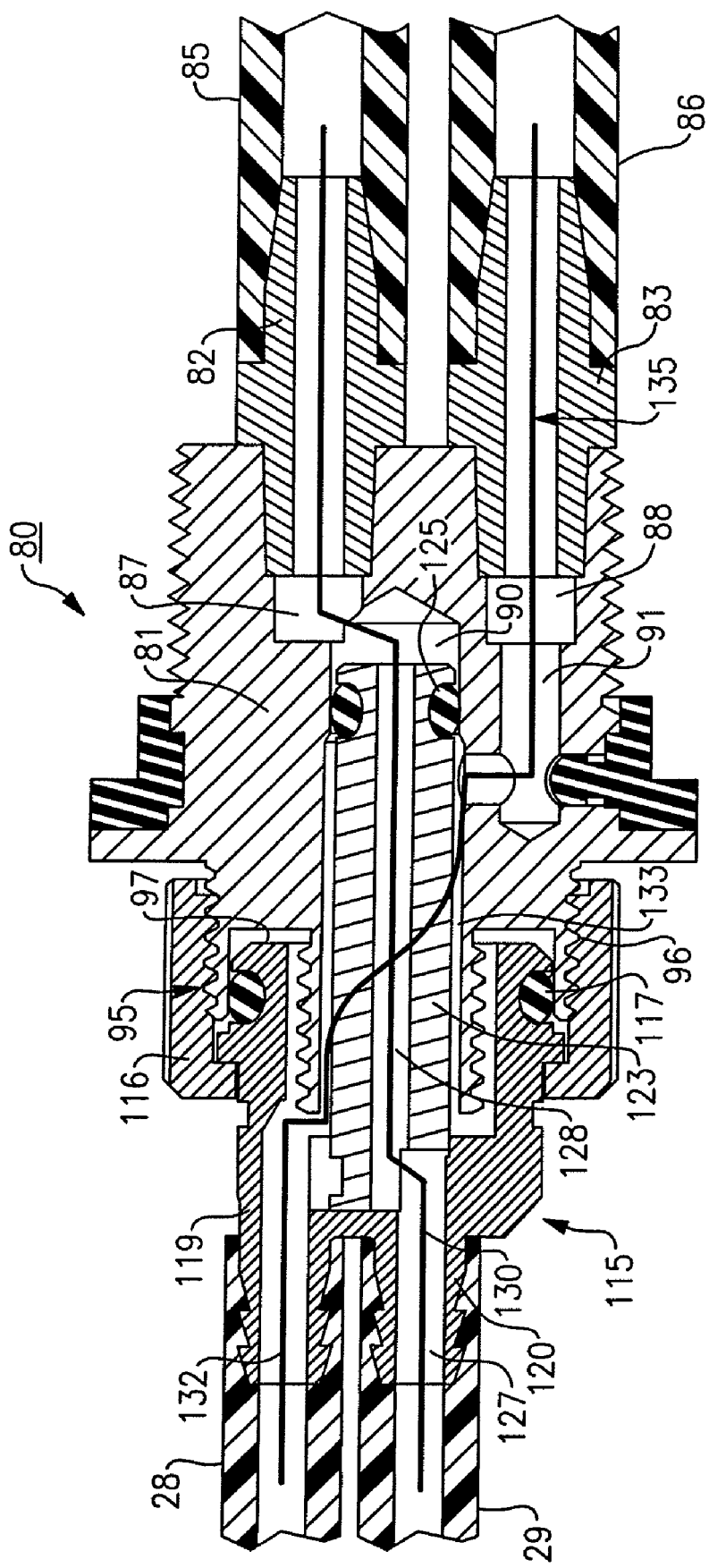
FIG. 9 is an enlarged side view in section showing the single lumen input terminal connected to a dual lumen cuff.

With further reference to FIG. 9, the terminal 80 is further able to threadably receive a second dual lumen connector, generally referenced 115. The dual lumen connector includes a rotatable cap 116 having internal threads that are arranged to mate with the external threads 96 formed on the flange 95 of the terminal body. An O-ring seal 117 is arranged to close in sealing contact against the inside surface of recess 97. A pair of hollow barbs 119 and 120 are mounted on one end of the connector and a cylindrical member 123 that is integral with the dual lumen connector extends into the blind hole 90 of the terminal body when the cap 116 is fully threaded onto the flange 95 of the terminal body. Lumen 28 is shown coupled to barb 119 and lumen 29 is shown coupled to barb 120. An O-ring seal 125 is mounted upon the end of the member 123 which, in assembly, seals in contact against the inner wall of the blind hole 90.

The opening 127 in barb 120 opens into an opening 128 formed in the member 123 which in turn, opens into hollow nipple 82 via blind hole 90 and cavity 87. A flow path 130 is thus established between one lumen of a dual lumen cuff and flow line 85 that leads to flow circuit 16 of the monitor. Opening 132 in barb 119 opens into a gap 133 between the member 123 and blind hole 90, which, in turn, opens into the opening in nipple 83 via channel 91 and cavity 88. A second flow path 135 is thus established between lumen 28 and flow line 85 of monitor flow circuit 17. Thus configuring the pneumatic flow system so that the pump 23 of flow circuit 17 will inflate the cuff through lumen 29 and bleed valve 25 in flow circuit 17 will deflate the cuff through lumen 29.

As should now be evident from the description above, monitors equipped with the single terminal will have special time saving advantages when used in relatively large medical facilities that are set up to service patients at a number of separate locations. In this type of facility all single lumen cuffs will be equipped with a single lumen connector 100 (FIG. 8), while all dual lumen cuffs will be equipped with a dual lumen connector 115 (FIG. 9). Accordingly, each type of cuff can be quickly coupled to a monitor and blood pressure has measurements taken quickly without the need for further input to the monitor without the danger of the technician making and connection errors.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

The invention claimed is:

1. A pneumatic system for measuring a patient's blood pressure when connected to either a single lumen cuff or a dual lumen cuff wherein said system includes:
    a blood pressure monitor having a first lumen terminal and a second lumen terminal;
    a first flow circuit connected to said first terminal that contains a first pressure sensor;
    a second flow circuit that contains a pneumatic pump for inflating a cuff and a bleed valve for deflating a cuff;
    a flow director means operatively associated with said second terminal having a first position for directing said pump discharge to said first circuit and isolating said second terminal when a single lumen is connected to first connector wherein said cuff is inflated through and deflated through said single lumen and cuff pressure is sensed by said first pressure sensor, and for automatically moving said flow director to a second position when a first lumen of a dual lumen cuff is connected to the first terminal and a second lumen of said dual lumen cuff is connected to said second terminal wherein said cuff is inflated and deflated through said second lumen and the cuff pressure is sensed by said first pressure sensor.

2. The pneumatic flow system of claim 1, wherein said flow director means includes a common port connected to said second circuit, a circuit port connected to said first circuit and a lumen port that is connectable to said second lumen of a dual lumen cuff and;

a valve means that is movable between a first position wherein said common port is in fluid flow communication with said circuit port and a second position wherein said common port is in fluid flow communication with said lumen port.

3. The pneumatic system of claim 2, wherein said flow director includes a housing and wherein said ports all communicate with a common channel extending between said circuit port and said lumen port.

4. The pneumatic system of claim 3, wherein said valve means includes a piston slidably contained within said channel for movement between said first and second positions.

5. The pneumatic system of claim 4, wherein said piston contains channels for directing the flow from the common port to said circuit port when said piston is in said first position and for directing said flow from said common port to said lumen port when the piston is in said second position.

6. The pneumatic system of claim 5, that further includes a biasing means for urging the piston into said first position.

7. The pneumatic system of claim 6, that further includes a sensing means for detecting when a second lumen is coupled to said second terminal and for moving the piston to said second position against the urging of the biasing means when a second lumen is coupled to said second terminal.

8. The pneumatic system of claim 6, wherein said biasing means is a spring.

9. A pneumatic system for measuring a patient's blood pressure when connected to either a single lumen cuff or a dual lumen cuff wherein said system includes:
   a blood pressure monitor having a first lumen terminal and a second lumen terminal;
   a first flow director coupled to said first terminal and a second flow director coupled to said second terminal;
   each of said flow directors having a housing containing a channel and a piston slidably contained within said channel between a first position and a second position, a first lumen port located at one end of said channel and a second circuit port located at the other end of said channel and a third center port located at the mid-section of the channel;
   said first end port of each flow director being connectable to either a single lumen cuff or a first lumen or a second lumen of a dual lumen cuff to determine a blood pressure;
   said center port of a first flow director being connected to a pneumatic pump for inflating a cuff and a bleed valve for deflating said cuff;
   said center port of a second flow director being connected to a pressure sensor for sensing pressure in said cuff;
   said second end port of said first flow director being connected to said pressure sensor and said second end port of said second flow director being connected to said pump and said bleed valve;
   each flow director having a biasing means for normally placing the piston in a first position wherein said central center port is connected to said second end port; and
   wherein each flow director further includes means for placing the piston in a second position wherein said first end port is connected to said center port when a lumen is connected to an associated lumen terminal.

10. The flow system of claim 9, wherein said bleed valve and said pump are contained in a first flow circuit along with a pressure sensor.

11. The flow system of claim 10, wherein said first pressure sensor is a pressure transducer.

12. The flow system of claim 10, wherein said second pressure sensor is a pressure transducer.

13. A pneumatic system for measuring a patient's blood pressure when connected to either a single lumen or a dual lumen cuff, wherein said system includes:
   a blood pressure monitor having a first lumen terminal and a second lumen terminal, each of the first terminal and the second terminal having a flow director associated therewith;
   each flow director having a first end port, a spaced apart second end port and a center port;
   said first end port of each flow director being connectable to either a single lumen cuff or a first lumen or a second lumen of a dual lumen cuff to determine a blood pressure;
   said center port of said flow director of said first terminal being connected to a pump for inflating a cuff and a bleed valve for deflating a cuff and the center port of said flow director of said second terminal being connected to a pressure sensor for sensing pressure in a cuff;
   said second end port of the flow director of said first terminal being connected to said pressure sensor and the second end port of the flow director of the second terminal being connected to said pump and said bleed valve;
   wherein each flow director includes a valve that is movable between a first position wherein said center port is in fluid flow communication with said second end port and a second position wherein the center port is in fluid flow communication with said first port; and
   wherein each flow director includes a central means for changing the valve position from said first position to said second position when a lumen is connected to said first port of said flow director and return said valve to said first position when said lumen is disconnected from said first port.

14. A blood pressure monitor for measuring a patient's blood pressure using either a single lumen cuff or a dual lumen cuff wherein said monitor includes:
   a housing that contains a first channel that is connected to a first flow circuit containing a first pressure sensor, and a second channel that is connected to a second flow circuit that contains a pneumatic pump for inflating a cuff, wherein said cuff is said single lumen cuff or said dual lumen cuff, and a bleed valve for deflating said cuff;
   an elongated blind hole formed in said housing, said first channel having a first port that opens into said blind hole and said second channel having a second port that opens into said blind hole, said first and second ports being spaced apart along the length of the elongated blind hole;
   a single lumen connector and a separate dual lumen connector that are both interchangeably connectable to said housing;
   said single lumen connector having a single flow passage that communicates with both said first and said second channels when said single lumen connector is connected to said housing,
   wherein said single passage communicates with said blind hole;
   said dual lumen connector having a first flow passage that communicates with said first channel and a second flow passage that communicates with said second channel when said dual lumen connector is connected to said housing,
   wherein said dual lumen connector includes an elongated member that is insertable into said blind hole when said dual lumen connector is coupled to said housing, said elongated member having a seal that divides said blind hole into two separate chambers, said first port being located in a first chamber and said second port being located in a second chamber;

a first coupling means for attaching a single lumen of said single lumen cuff to said single lumen connector; and a second coupling means for coupling a first lumen of said dual lumen cuff to said first passage of said dual lumen connector and a second lumen of said dual lumen cuff to said second passage of said dual lumen connector.

15. The monitor of claim 14, wherein the first flow passage of said dual lumen connector communicates with said first chamber and said second flow passage of said dual lumen connector communicates with said second chamber when said dual lumen connector is attached to said housing.

* * * * *